(12) United States Patent
Fox

(10) Patent No.: US 6,325,806 B1
(45) Date of Patent: *Dec. 4, 2001

(54) MATERIALS COLLECTION SYSTEM AND USES THEREOF

(75) Inventor: William Casey Fox, Pipe Creek, TX (US)

(73) Assignee: BioMedical Enterprises, Inc., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/494,872

(22) Filed: Jan. 31, 2000

Related U.S. Application Data

(63) Continuation of application No. 08/799,122, filed on Feb. 11, 1997, now Pat. No. 6,071,284, which is a continuation-in-part of application No. PCT/US96/03875, filed on Mar. 22, 1996.
(60) Provisional application No. 60/042,774, filed on Oct. 30, 1995.

(51) Int. Cl.⁷ .................................................. A61B 17/16
(52) U.S. Cl. ............................................. 606/80; 606/102
(58) Field of Search .................................. 606/79–86, 53, 606/102, 96; 604/4, 187

(56) References Cited

U.S. PATENT DOCUMENTS

| | | |
|---|---|---|
| 2,526,662 | 10/1950 | Hipps et al. . |
| 3,466,693 | 9/1969 | Grant ................................... 15/210 |
| 3,749,084 | 7/1973 | Cucchiara . |
| 4,111,208 | 9/1978 | Leuenberger . |
| 4,481,946 | 11/1984 | Altshuler et al. ........................ 604/4 |

(List continued on next page.)

FOREIGN PATENT DOCUMENTS 3007036    9/1981    (DE) .

1465033 A1    3/1989    (RU) .

(List continued on next page.)

OTHER PUBLICATIONS

Altman et al., "Use of the Bone Biopsy Trephine to Obtain Iliac Crest Cancellous Bone," *J. Oral Maxillofac. Surg.* 52:522–523 (1994).
Burchardt et al., "Transplantation of Bone," *Surgical Clinics of North America* 58(2):403–427 (1978).
Catone et al., "Tibial Autogenous Cancellous Bone as an Alternative Donor Site in Maxillofacial Surgery: A Preliminary Report," *J. Oral Maxillofac. Surg.* 50:1258–1263 (1992).
Damien et al., "Bone Graft and Bone Graft Substitutes; A Review of Current Technology and Applications," *J. Applied Biomaterials*, 2:187–208 (1991).

(List continued on next page.)

*Primary Examiner*—David O. Reip
(74) *Attorney, Agent, or Firm*—Akin, Gump, Strauss, Hauer & Feld, L.L.P.

(57) ABSTRACT

The present invention relates to instrumentation and uses thereof for collection of cuttings from cutting tools. Cuttings may be from precious metals, toxic or hazardous substances, or from living tissue such as bone. In a particular embodiment of collecting bone cuttings, the present invention includes instrumentation used with a drill bit so that bone cuttings (195) are aseptically collected in a collection chamber (110) for subsequent transplantation purposes. When in use, marrow and bone cuttings (195) are drawn into the flutes (170) of a drill bit (150), carried up the bore of the instrument tip (100) and collect in the collection chamber (110). The flutes of the drill bit (150) can be cleared of residual tissue through the use of a rotating flute wiper (160) that rotates with the drill bit (150) when drilling or when the drill bit (150) is withdrawn from the instrument. In this embodiment, use of the device allows collection of vital bone tissue for reconstruction of bone defects, fractures, or fixation of orthopedic or dental implants that contact bone.

30 Claims, 11 Drawing Sheets

U.S. PATENT DOCUMENTS

| | | | |
|---|---|---|---|
| 4,486,188 | 12/1984 | Altshuler et al. | 604/4 |
| 4,649,919 | 3/1987 | Thimsen et al. . | |
| 4,844,064 | 7/1989 | Thimsen et al. . | |
| 4,991,452 | 2/1991 | Dillard et al. | 73/864.44 |
| 5,064,425 | 11/1991 | Branemar, et al. | 606/72 |
| 5,078,553 | 1/1992 | Dutkiewicz et al. . | |
| 5,199,942 | 4/1993 | Gillis | 604/4 |
| 5,269,785 | 12/1993 | Bonutti | 606/80 |
| 5,385,570 | 1/1995 | Chin et al. | 606/170 |
| 5,403,317 | 4/1995 | Bonutti | 606/80 |
| 5,407,425 | 4/1995 | Werner et al. | 604/4 |
| 5,443,468 | 8/1995 | Johnson | 606/80 |
| 5,451,227 | 9/1995 | Michaelson | 606/3 |
| 5,562,673 | 10/1996 | Koblish et al. . | |
| 5,591,187 | 1/1997 | Dekel | 606/180 |
| 5,632,747 | 5/1997 | Scarborough et al. . | |

FOREIGN PATENT DOCUMENTS

| | | |
|---|---|---|
| 1521464 A1 | 11/1989 | (RU) . |
| 1584916 A1 | 8/1990 | (RU) . |
| 1644923 A1 | 4/1991 | (RU) . |
| 1725858 A1 | 4/1992 | (RU) . |
| WO 97/16118 | 5/1997 | (WO) . |

OTHER PUBLICATIONS

W. Dick, "Use of the Acetabular Reamer to Harvest Autogeneic Bone Graft Material: A Simple Method for Producing Bone Paste," *Arch. Orthop. Trauma Surg.* 105:235–238 (1986).

Dumbach et al., "Mandibular Reconstruction with Cancellous Bone, Hydroxylapatite and Titanium Mesh," *J. Cranio–Maxillo–Facial Surg.* 22:151–155 (1994).

Hall et al., "Comparative Anatomic Study of Anterior and Posterior Iliac Crests as Donor Sites," *J. Oral Maxillofac. Surg.* 49:560–563 (1991).

Holzmuller et al., "Harvesting Small Amounts of Autogenous Spongiosa with a New Set of Instruments," *Unfallchirurg* 98(2):59–62 (Feb. 1995).

Krause et al., "Distal Femur as a Donor Site of Autogenous Cancellous Bone Graft," *J. Orthop. Trauma* 9(2): 145–151 (Mar./Apr. 1995).

Marx et al., "Cellular Survival of Human Marrow During Placement of Marrow–Cancellous Bone Grafts," *J. Oral Surgery* 37:712–718 (1979).

McGurk et al., "The Trephining of Bone from the Iliac Crest: an Anterior Approach," *J. Oral. Maxillofac. Surg.* 22:87–90 (1993).

O'Keeffe et al., "Harvesting of Autogenous cancellous Bone Graft from the Proximal Tibial metaphysis—A Review of 230 Cases," *J. Orthop. Trauma* 5(4):469–474 (1991).

Ripamonti et al., "Growth and Morphogenetic Factors in Bone Induction: Role of Osteogenin and Related Bone Morphogenetic Proteins in Craniofacial and Periodontal Bone Repair," *Critical Reviews in Oral Biology and Medicine* 3(1/2): 1–14 (1992).

Rosen et al., "The BMP Proteins in Bone Formation and Repair," *TIG* 8(3):97–102 (1992).

Schwarz et al., "Fresh Autogeneic, Frozen Allogeneic, and Decalcified Allogeneic Bone Grafts in Dogs," *J. Bone and Joint Surgery*(Br.) 73–B:787–790 (1991).

Setz et al., "Autogenous Bone Marrow and Allograft Replacement of Bone Defects in the Hand and Upper Extremites," *J. Orthop. Trauma* 6(1):36–42 (1992).

Shumrick et al., "The Use of Cancellous bone for Frontal Sinus Obliteration and Reconstruction of Frontal Bony Defects," *Arch. Ololaryngol. Head Neck Surg.* 120:1003–1009 (1994).

Trevor et al., "Evaluation of the Proximal Portion of the Femur as an Autogenous Cancellous Bone Donor Site in Dogs," *Am. J. Vet. Res.* 53(9):1599–1603 (1992).

Wagner et al., "The Use of Cylindrical Osteotomes for Harvesting Cancellous Bone from the Ilium," *J. Oral Maxillofac. Surg.* 49:433–437 (1991).

Dialog Search, Feb./Mar. 1996.

PCT/US96/03875 International Search Report mailed Aug. 14, 1996.

Biomedical Enterprises, Inc., Advertisement/Product Description for Bone and Marrow Collection System™, Feb. 1, 1997.

European Search Report dated Nov. 4, 1999 for European Application No. 96911365.3.

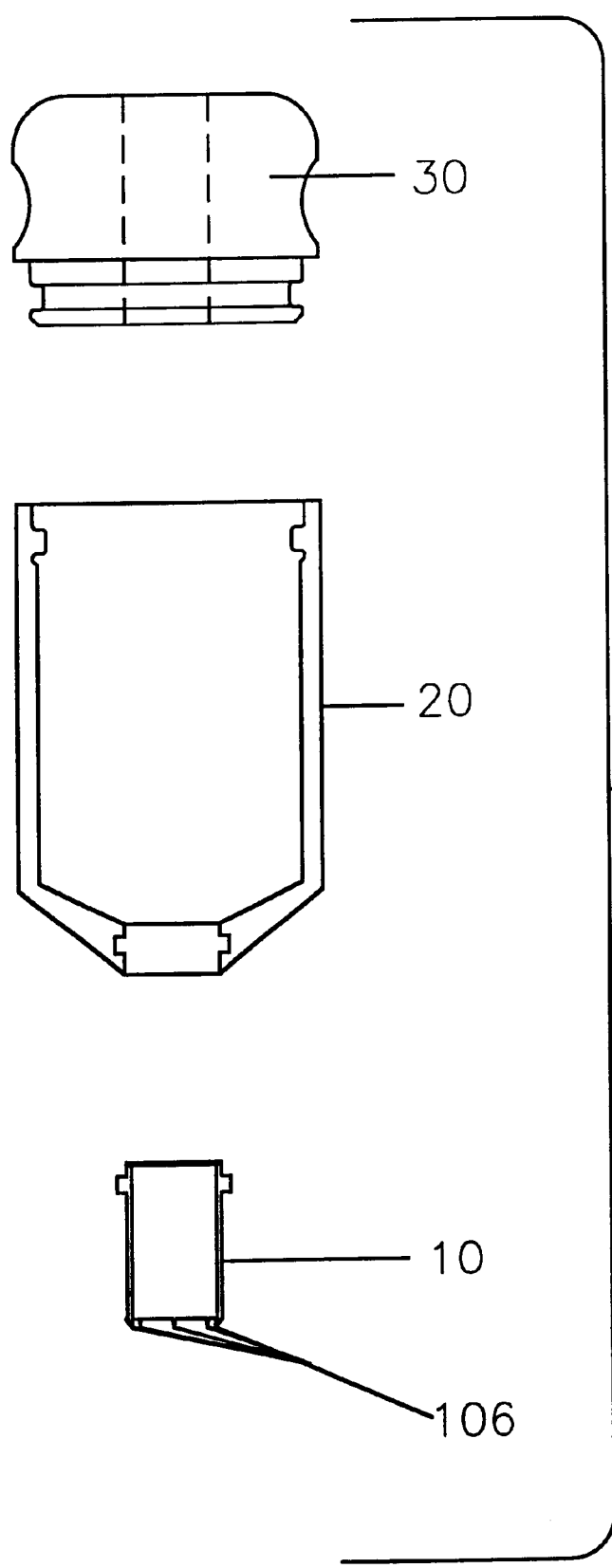

MATERIALS COLLECTION SYSTEM AND USES THEREOF

The present application is a continuation application of U.S. Ser. No. 08/799,122 filed Feb. 11, 1997, now U.S. Pat. No. 6,017,284, which is a continuation-in-part application of PCT/US96/03875 filed Mar. 22, 1996 which claims the benefit of U.S. Ser. No. 60/042,774 filed Oct. 30, 1995, now abandoned.

FIELD OF THE INVENTION

The present invention relates to fields of use where cuttings are collected from the action of a cutting tool. Instrumentation and methods are provided for industrial and medical applications. In particular, the present invention relates to surgical instrumentation and a method of use that allows skeletal tissue collection. Furthermore, collected skeletal tissue may be processed and transplanted, preferably within the donor subject to provide an autologous transplant.

BACKGROUND OF THE INVENTION

In the production of machine parts to meet standard requirements for the U.S. military, the U.S. Food and Drug Administration, and the International Organization for Standards; cuttings resulting from machining processes are collected and returned to inventory control to account for all material issued to the shop floor. To account for all issued materials; scrap cuttings, residual bulk material, and machined parts are weighed to ensure that no unidentified materials are uncontrolled on the shop floor. Scrap cuttings from high-grade medical or military specification materials are expensive and, therefore, cost effective to recycle. In another example of collection of cuttings, jewelers collect and recycle materials that fall in the work area during the machining of precious materials such as gold and silver.

The surgical harvest of bone, with or without marrow components, is a further example of the need for instrumentation for collection of cuttings. Harvested bone material is used in treatment of bone defects and diseases. The goal of therapeutic transplantation of bone and bone marrow products is the induction or augmentation of bone growth and repair at a defect site or around an implant site.

Autogenous bone grafts are the gold standard against which all graft materials are measured. Acquisition of fresh autogenous bone transplant material provides all naturally available mitogens and growth factors in physiologic concentrations, viable mesenchymal and progenitor cell populations, and natural bone matrix. Autograft bone has greater osteogenic capacity than either allograft bone (tissue from donors of the same species) or xenograft bone (tissue from donors of different species). In comparison to frozen allogenic and decalcified allogenic bone, fresh autogenic cancellous bone grafts lead to healing in most instances. Autogenous bone grafts avoid the potential immunologic and infectious complications associated with allograft materials.

Attempts to reduce morbidity associated with cancellous bone harvest have used minimally invasive surgical techniques, including use of cylindrical osteotomes that allow for the harvest of several bone plugs obtained through a single initial cortical entrance. This technique is slow and obtainable bone volume is limited. Bone biopsy trephines offer an advantage in that no muscle or ligamentous attachments are disturbed, but again, the technique limits harvest volume and shape, and collection of the harvested material is tedious.

Other techniques have used square- or rectangular-shaped bone windows that contribute to major donor-site morbidity. Angular defects produced in the formation of common bone windows weaken bone structure because fractures can be propagated from the corners of such defects.

Devices and systems for bone cutting, and bone marrow tissue aspiration and processing for transplantation have been previously described. Bonutti (U.S. Pat. No. 5,269,785, U.S. Pat. No. 5,403,317) and Thimsen et al. (U.S. Pat. No. 4,649,919, U.S. Pat. No. 4,844,064) relate to orthoscopic tissue removal. Johnson (U.S. Pat. No. 5,443,468) and Leuenberger (U.S. Pat. No. 4,111,208) relate to drill bits and drill motor attachments; Abtopckomy (SU 1644923 A1), Zelenov (SU 1066578), and Michaelson (U.S. Pat. No. 5,451,277, and WO 9505123) relate to a bone tissue cutting device; and Chin (U.S. Pat. No. 5,385,570) relates to a surgical cutting instrument with a recess for collecting chips of material. Bone marrow transplant methods and apparatus were described by Werner (U.S. Pat. No. 5,407,425), Gillis (U.S. Pat. No. 5,199,942) and Altshuler (U.S. Pat. Nos. 4,486,188 and 4,481,946).

Grant (U.S. Pat. No. 3,466,693) relates to the active wiping of drill pipe for oil field use, and Dillard (U.S. Pat. No. 4,991,452) relates to a sampler for hazardous solid materials.

The apparatus of Soviet Patent SU 1725858 lacks a closed channel between bone chip removal channels of the needle and the spring-loaded tube, the needle is fixed, and further, the device is completely dependent upon use with a needle.

Existing cuttings collection instrumentation fails to take into account the need for custom design for specific applications, the need for facile quantitation of collected material, the need for efficient transport to a second site, or the need for aseptic conditions or environments having lowered oxygen levels, for example. In particular, existing skeletal harvesting instrumentation and transplanting methods have encountered significant problems due to material characteristics and bone material harvest techniques employed. Existing methods and associated deficiencies include: 1) genetically foreign bone and bone matrix often elicit an inflammatory response and immunogenic rejection, 2) freeze-dried bone implants from human donors are slow to vascularize and pose unacceptable risks of postoperative complications including disease transmission, 3) second-site surgery in the patient to obtain autografts often result in high morbidity and complications, 4) cortical bone implants are difficult to shape and conform to a defect site, 5) present bone harvest instrumentation and equipment are limited to trephines and curettes and limit quantity and quality while requiring second-site surgery, and 6) a deficiency exists in present synthetic bone matrix materials, such as compositions of calcium phosphate and calcium carbonate, silica glass, copolymers of polylactic and polyglycolic acid, and sea coral.

Because these prior art techniques are not completely satisfactory, the present inventors have searched for improvements and provide the invention described herein.

SUMMARY OF THE INVENTION

The present invention provides an instrument and methods for the collection of cuttings that result from the cutting action of tools. The instrument comprises a tip adapted for use with a cutting tool, and a collection chamber attachable to the tip for collecting and holding cuttings. When a cutting tool is inserted through the instrument, and when in use, the instrument acts independently from the cutting tool by allowing cutting tool rotation along its longitudinal axis and translation of the cutting tool in and out through the instrument so as to channel, pull, or fling cuttings for accumulation in the collection chamber.

By "adapted for use with a cutting tool" is meant that the tip serves as a cutting tool guide, and can further serve as a cutting tool bearing. The tip has a bore for fitting to a cutting tool having a flute. When fitted with a cutting tool having a flute, the tip and the flute form an enclosed channel. Aspects of the invention that cause the accumulation of cuttings in the collection chamber include channeling from the action of a cutting tool, pulling due to translation of the cutting tool, and flinging due to centripetal forces caused by rotation of the cutting tool. An enclosed channel between tip 10 and a flute of a cutting tool as shown in FIG. 1 of the present specification necessarily provides the forces of axial pumping to move material. Axial pumping includes radial forces, translational forces, and use of suction.

An embodiment of the instrument further comprises a cap attachable to the collection chamber, the cap adapted for use with a cutting tool. By "adapted for use with a cutting tool" is meant that the cap serves as a cutting tool guide, and further may serve as a cutting tool bearing. A cap may have a bore for fitting to a cutting tool, it may have a further attachment for mixing contents of the attachment with cuttings in the collection chamber.

In another embodiment of the present invention, the instrument may further comprise a wiper for wiping a cutting tool. The wiper may have a flexible or rigid protrusion, and may be fittable into a wiper bushing that is attachable to the collection chamber or to the cap. The protrusion for wiping a cutting tool may be flexible so as to contour to the cutting tool surface, such as a wire, a bristle, or a brush; or the protrusion may be rigid and formed to matchingly fit or contour to a flute or cross-sectional outline of a drill bit. The protrusion for wiping a cutting tool may further consist of a finger that runs against the outside of the cutting tool to clear material and may be located near the junction of the tip and collection chamber.

Aspects of further embodiments of the invention that contribute to accumulation of cuttings in the collection chamber include the use of a wiper as herein described and use of suction from a vacuum line, for example. These aspects add the actions of wiping and sucking to the previously described actions of channeling, pulling, and flinging as means by which the present invention provides for the collection of cuttings resulting from the use of cutting tools.

The tip of the instrument may further comprise a tooth or a plurality of teeth for eliminating slippage on a cutting surface. The tip may be a spherical tip or a swivel tip.

In a preferred embodiment of the invention, the instrument further comprises a concentrically oriented cutting tool. By "cutting tool" is meant a tool having a flute such as a drill bit, bur, grinder, rasp, reamer, milling cutter, fluted trocar, fluted hole saw, or the like. By "concentrically oriented" is meant that the tool fits into the body of the instrument or an extension of the instrument so as to be substantially centered within the instrument or within the extension of the instrument. The cutting tool may be fitted with an adjustable stop, preferably with a calibrated adjustable stop.

In a further preferred embodiment of the instrument of the invention having a cutting tool, the cutting tool is a drill bit. The drill bit may have a standard tip; or a tip with a first side and a second side, the first side having a straight cutting edge, and the second side having a row of grinding teeth; but is not limited thereto.

The cutting tool may be rotated manually, however, the instrument may further comprise a mechanism for rotating the cutting tool for optimizing the cutting action for hardened materials such as metal. A preferred mechanism is an external motor.

In another aspect of the invention, the instrument further comprises an attachment for pushing cuttings out of the collection chamber through the tip for application to a site. The attachment may be a plunger that is inserted through the cap. In another aspect, the attachment may be a dual plunger that is inserted into the collection chamber after the cap has been removed.

The collection chamber may further comprise a means for measuring volume. In an embodiment, the collection chamber has a transparent or translucent wall and the means for measuring volume includes a volumetric marking on the wall. Such an instrument may further comprise a plunger for packing collected cuttings so that packed volume may be measured.

Certain of the parts of the instrument may be advantageously fabricated as one unit so as to provide a disposable unit, for example. Such units may include the tip, the collection chamber, and a wiper bushing; the tip and the collection chamber; or the cap, a wiper, and a wiper bushing.

A drill bit having a tip with a first side and a second side, the first side having a straight cutting edge, and the second side having a row of grinding teeth is a further aspect of the present invention. Cuttings obtained by a process of using the instrument fitted with a cutting tool having said drill bit is another aspect of the invention.

In a further embodiment of the instrument of the present invention, the collection chamber further comprises an opening for connection to a vacuum line to provide suction.

In an embodiment of the invention, skeletal tissue is harvested using the instrument provided. In a further preferred embodiment, the harvesting is performed aseptically so as to provide material for transplant. By "skeletal tissue" is meant bony or more or less cartilaginous framework of an organism, bone, bone marrow, cartilage, ligaments, spongy bone tissue, or tendon, including intrinsic physiological factors thereof, such as growth factors, blood, biochemical or cellular components or constituents. By "aseptic conditions" is meant those sterile or near sterile conditions as operative in a surgical setting. As one of skill in the art would realize upon reading this disclosure, aseptic would include sterilization of instruments, surfaces, solutions, and the like; use of sterile garments, masks, and the like; and filtering of ambient air, for example. Sterilization may be achieved by heat, ultraviolet light, alcohol swabbing, or use of germicides, for example.

A materials transplant system is another embodiment of the present invention. The system comprises an instrument of the present invention with or without a wiper, fitted with a cutting tool, and means for moving cuttings to an alternate site of use, such as a site of implantation. In an embodiment, the cuttings are bone cuttings and the system is a sterile tissue transplant system. The materials transplant system may further comprise means for processing tissue, such as an encapsulation nozzle, for example. By "means for moving cuttings to an alternate site of use" is meant any means of transporting cuttings from the site of harvest to a different site.

A method or use of a materials transplant system as described herein for aseptically transplanting skeletal tissue from a first site to a second site is another embodiment of the invention. The method includes the steps of removing skeletal tissue aseptically from the first site using the materials transplant system herein described, and implanting the skeletal tissue aseptically at the second site. The skeletal tissue may be processed before implanting at the second site, and the processing may include washing, grinding, tissue separation, acid addition, base addition, encapsulant addition, or therapeutic agent including but not limited to pharmaceutical and growth factor addition. In particular, the first site and the second site are within one subject so that the implant is an autologous transplant. In use of the present invention, the bioptate has a high surface area which makes the bioptate tissue especially useful and effective in transplantation.

The instrument of the present invention is useful in any field of use where cuttings are collected. Cuttings may be collected because the materials being cut are precious, i.e., rare, expensive, or have a special property, and where loss is undesirable. On the other hand, cuttings may be toxic or hazardous, and collection of such cuttings is desirable to minimize any hazard. Toxicity may be due to volatility, flammability, radioactivity, or due to biohazardous aspects, such as having a virus like the HIV virus, for example.

In the machining of hazardous materials, the instrument and methods of the present invention provide enhanced safety. Materials that are easily oxidized and present a fire hazard such as titanium, magnesium, and sodium can be collected safely in the system since oxygen pressure can be controlled within the system. The design of the instrument minimizes any fire hazard by having a reduced access to oxygen in a substantially closed system. Vacuum can be used to remove powdered cuttings and further reduce collection chamber oxygen tension. Furthermore, the collection system may be flushed with an inert gas such as argon, for minimizing combustion hazard.

In industrial applications, gold, silver, platinum, or uranium can be machined and the cuttings can be collected for reuse, disposal, or to address safety or environmental concerns, for example. The instrument may also be used in a microgravity environment for the collection of cuttings that would not otherwise be contained. By "microgravity" is meant any environment having a force of gravity less than that found on the surface of the earth, for example, the space station environment.

In medical applications, the collection of cuttings of skeletal tissue is particularly contemplated in orthopaedic or dental applications where bone and/or marrow is to be drilled or aseptically harvested for subsequent medical use. Harvested skeletal tissue may be used for transplants, for facilitating healing of bone defects, or for assisting implant acceptance. If harvested tissue is a biohazard, the present collection system enhances the safety of handling such tissue by keeping it substantially contained until disposal.

Particular materials contemplated by the inventor for cutting with the instrument of the present invention include skeletal tissue, metals, ceramics, and polymers. By "ceramic" is meant a material made of silica-based ceramic, silica glass, calcium carbonate, calcium phosphate, hydroxyapatite, porcelain, or an aerospace ceramic, for example. By "aerospace ceramic", is meant materials such as fibrous refractory composite insulation, thermoplastic syntactic foam, ceramic matrix composite, or the like. By "polymer" is meant medical grade polymers such as polymethylmethacrylate, polycarbonate, polystyrene, polyvinylchloride, silicone elastomer, or the like.

The instrument of the present invention can be used by following the steps of an exemplary orthopaedic procedure as follows: 1) place the instrument on bone, to locate the cutting site, and provide a guide for the cutting tool, in this example, a drill bit, 2) place the drill bit into the instrument, 3) drill in a manner consistent with clinical practice, 4) withdraw the drill from the instrument, 5) hold the instrument at the drill site so as to align the bore of the tip and drill hole to allow marrow tissues including blood to well up into the tip and collection chamber, 6) remove the instrument from the site, 7) compact the harvested material within the instrument, 8) measure the volume of material collected, 9) extrude compacted material through the tip or withdraw it from the bore of the collection chamber, and 10) implant the material in a second site within the same patient.

In this ten step example, the independence of the instrument from the drill bit is demonstrated in noting that the drill bit was used with the instrument in only three steps (2, 3 and 4), tissue was collected in three steps (3, 4 and 5) and tissue was manipulated within the device in 6 steps (3, 4, 5, 6, 7, 8 and 9). In this example, in addition to collecting tissue, the instrument was used to locate the site of drilling, brace the drill, guide the drill, control the depth of drilling through use of an adjustable stop, protect surrounding tissues from being caught by the edge of the drill, and to collect, protect, store and transport tissue in a sterile manner.

Advantages of the present invention include: 1) the instrument can be customized to specific cutting procedures and requirements, 2) the instrument facilitates rapid and easy volumetric quantitation of collected material, 3) the instrumentation facilitates the efficient utilization and placement of collected cuttings in an alternate site, 4) the invention eliminates the practice of discarding and waste of valuable materials, 5) the invention can be used with conventional drill motors and bits, 6) the invention efficiently combines three processes: channeling, pulling, and slinging to collect cuttings, 7) the invention is adaptable to numerous types of cutting tools, 8) the invention can be used to collect precious metal chips and dust, 9) the invention can be used to automatically collect radioactive material, 10) the invention can be used to reduce the likelihood of a fire when cutting oxidizable materials, 11) the invention can be used to locate and brace a cutting tool, 12) a flute wiper of the invention can rotate with the bit during rotation and translation, 13) the instrument can be held by hand, 14) the invention is independent from the cutting tool in many of its uses, and 15) efficient collection through the processes of channeling, pulling, and flinging can be further enhanced by adding the processes of wiping and suctioning.

Further advantages of the present invention that are apparent in the application of harvesting skeletal tissue include: 1) the invention allows harvest of cancellous and other bone and/or marrow material from multiple donor sites, 2) the invention allows for optimal processing of viable collected skeletal tissue for transplantation by providing it in small pieces with a high surface area and washed in vital marrow elements, 3) the invention minimizes biohazards associated with the disposal of human bone cuttings, 4) the invention decreases patient morbidity by decreasing harvest time and allows the use of minimally invasive surgical procedures, and 5) the invention decreases mechanical stress concentration and probability of iatrogenic fracture and morbidity.

Following long-standing patent law convention, the terms "a" and "an" mean "one or more" when used in this application, including the claims.

BRIEF DESCRIPTION OF THE DRAWINGS

Further objects and advantages of this invention will become apparent from consideration of the drawings and ensuing description of the preferred embodiments.

FIG. 2 shows an exploded plane view with some components in cross-section of an embodiment of the invention.

LIST OF REFERENCE NUMERALS

Figure 1:
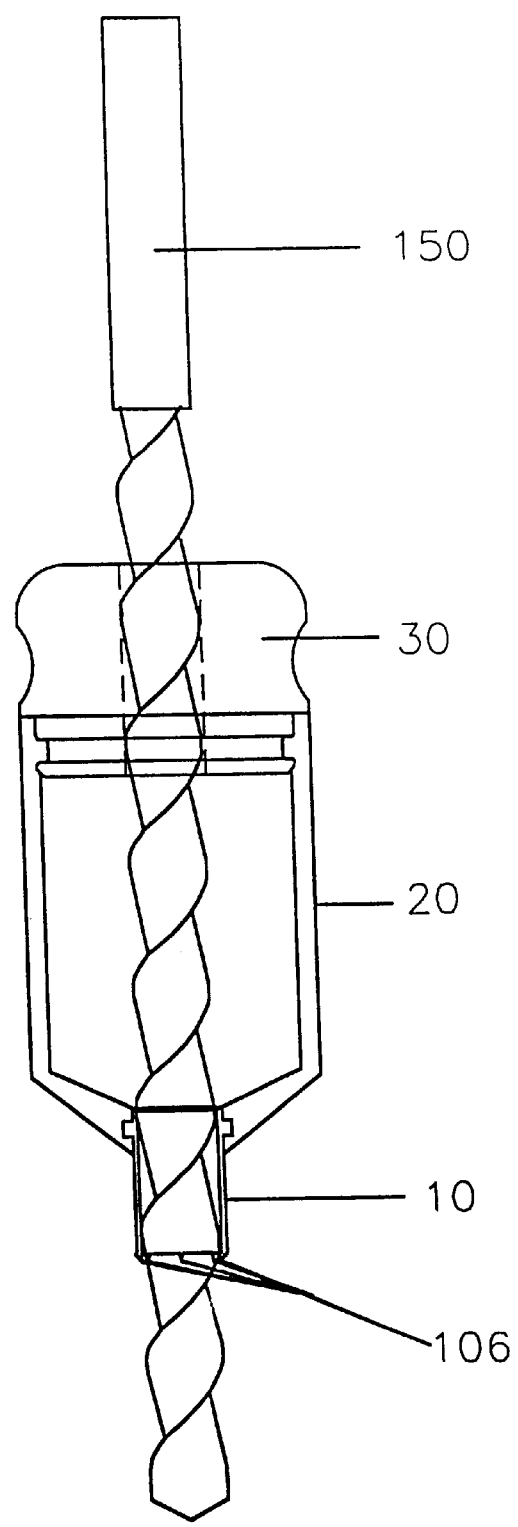
FIG. 1 shows a cross-sectional plane view of an embodiment of the instrument of the present invention having a drill bit placed therein.

10, 100 tip
103 spherical end tip
105 means for measuring volume
106 tip teeth
20, 110 collection chamber
120 wiper bushing
130 drill wiper
30, 140 cap
150 drill bit
160 flute wiper
170 drill flute
180 swivel tip
183 tip fixation prongs
186 swivel tip teeth
190 cancellous bone
193 cortical bone
195 bone cuttings
200 cutting edge
210 grinding teeth
220 land
230 flute
240 drill shank
250 adjustable stop
401 collection chamber
402 tissue suction line
403 tissue reservoir
404 vacuum pump
405 bone cuttings
406 roller pump
407 tissue separator
408 valve
409 encapsulant
410 encapsulation nozzle
411 applicator
412 encapsulated tissue
413 bone
414 iliac crest
500 tip plunger
510 collection chamber plunger
520 plunger head
530 plunger face
540 collection chamber extrusion face
600 drill flute wiper
610 drill flute protrusion
620 generic wiper
630 generic wiper protrusion
640 reamer flute wiper
650 reamer flute protrusion
700 suction port
710 handle
720 suction relief hole
730 baffle
740 collection chamber
750 collection chamber extension
760 wiper
770 bushing cap
780 tip
800 suction port
810 suction attachment
820 baffle
900 suction port
910 suction attachment
920 filter
930 seal ring

DETAILED DESCRIPTION OF THE PREFERRED EMBODIMENTS

The present invention, in one example of its preferred embodiment, provides surgical instrumentation that acts as a cutting tool brace for efficient cutting and collection of skeletal tissue, including bone and cartilage tissue. The invention further provides for transfer of harvested tissue to an implantation site. When the harvest site and implantation site are within the same subject, the transplant is called an autologous transplant or an autograft. This type of transplant is as close to ideal as can be achieved, since intrinsic growth factors and matrix material are provided, and the possibility of immune rejection is avoided. When the harvest site and implantation site are in different subjects, the transplant is called an allogeneic transplant or allograft, and the possibility of immune rejection by the recipient subject exists. An implantation site may be a structural defect or a site of an implant in a bone or cartilaginous site in a body, such as an orthopaedic implant or dental implant.

Freshly harvested bone or cartilage tissue can be described as being vital and having inductive potential. This means that freshly harvested tissue has growth factors and matrix material that, when implanted in the donor patient, stimulate bone or cartilage to heal. Exemplary intrinsic growth factors and matrix material include, but are not limited to, transforming growth factor beta, fibroblast growth factor, bone morphogenetic proteins, biocompatible scaffolding, and natural matrix material to facilitate bone to bridge large fractures or fill defects. Growth factors, such as these and others, are contemplated as optionally being added to harvested material to further enhance bone healing at an implant site.

Figure 3A:
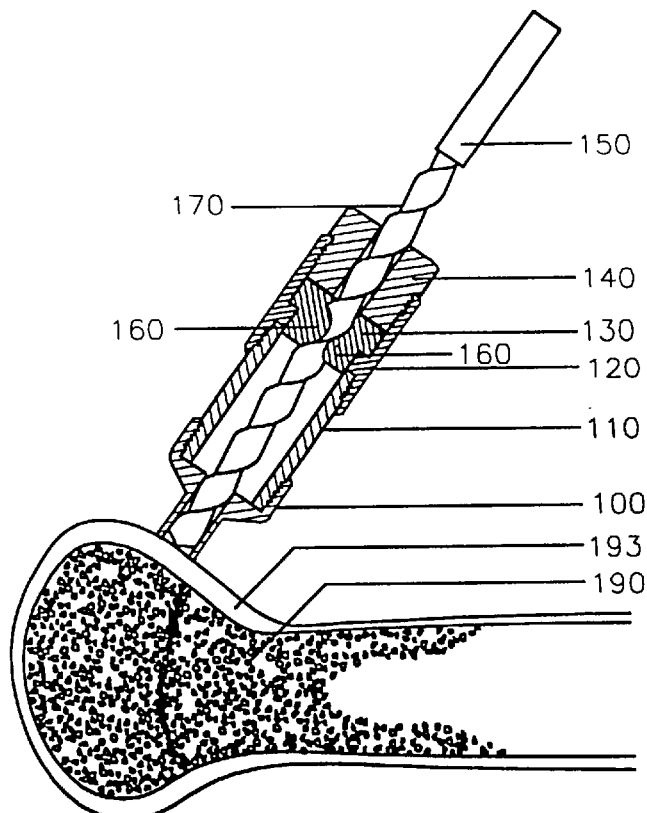
FIG. 3a shows a cross-sectional plane view of a further embodiment of the invention adjacent to bone and prior to drilling.
Figure 3B:
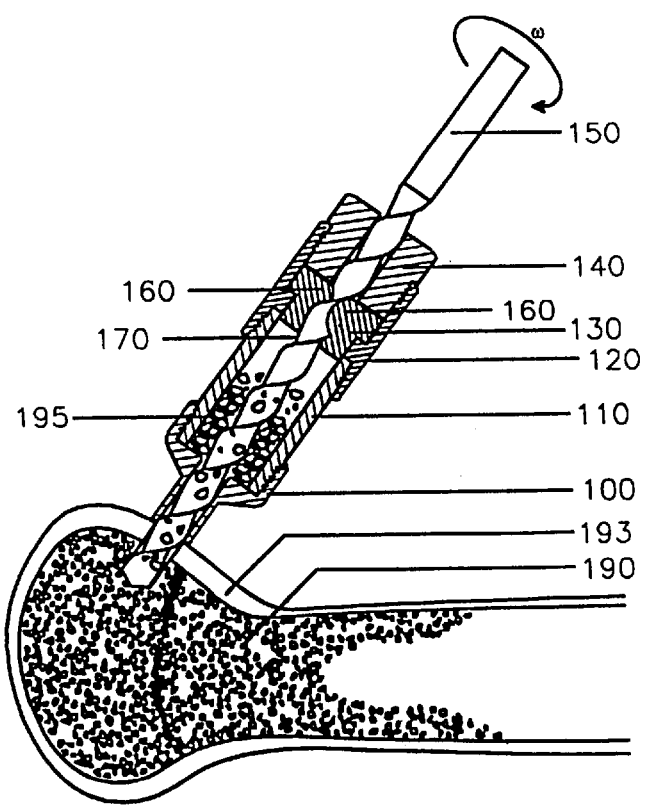
FIG. 3b illustrates an embodiment of the invention during a harvesting operation. The drill body (150) is being rotated at speed (w) in a clockwise direction.
Figure 4A:
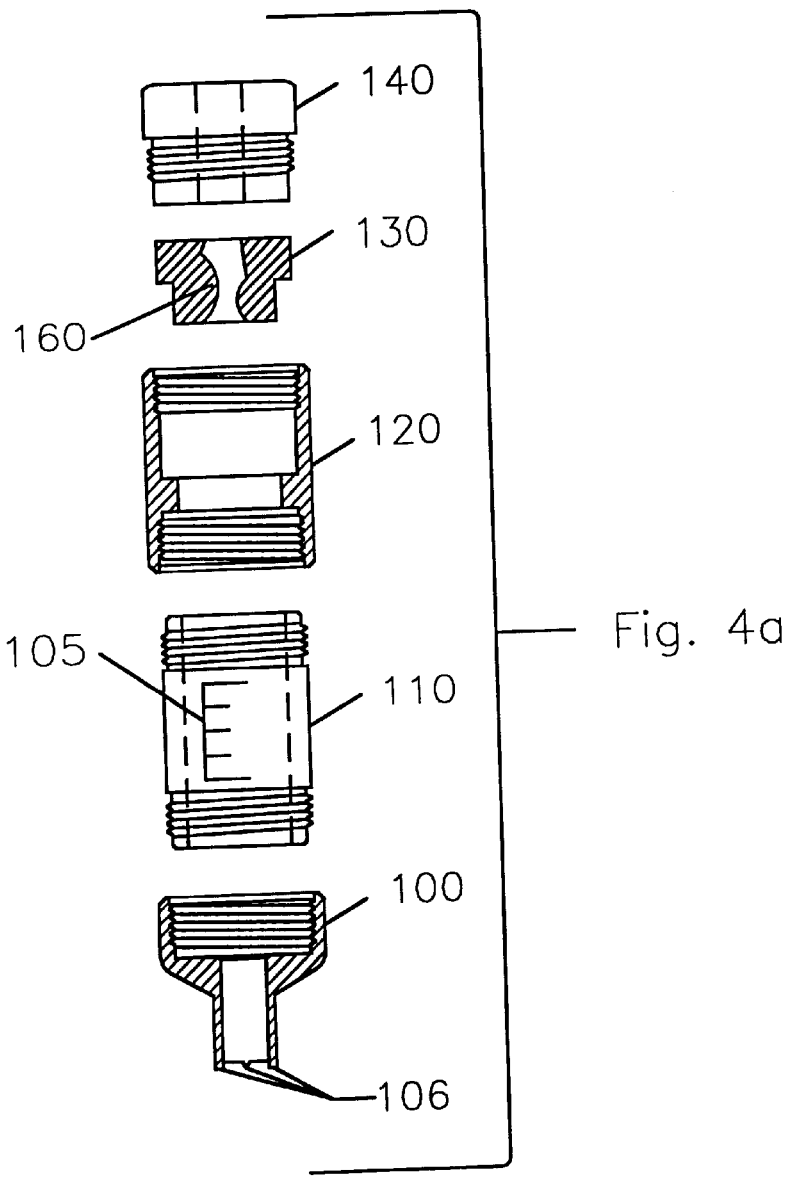
FIG. 4a shows an exploded plane view with some components in cross-section of an embodiment of the invention.
Figure 4B:
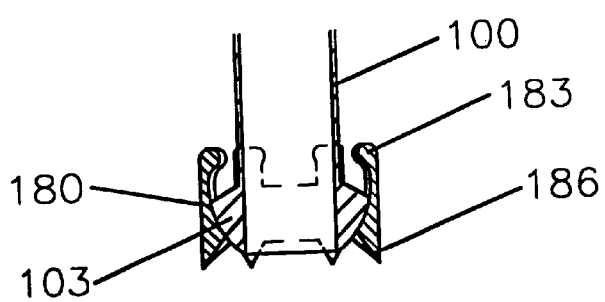
FIG. 4b shows a plane view of a tip of an instrument with means to grip bone surface and pivot to provide a seal between the tip and bone.

In a preferred embodiment of FIG. 1 and FIG. 3a, a surgical instrument of the present invention allows aseptic collection of bone and cartilage cuttings and comprises a tip (10, 100) that contacts bone and guides a cutting tool, a collection chamber (20, 110) that collects and holds bone cuttings, and a cap (30, 140) having a bore that acts as the upper cutting tool (150) guide and bearing. Together the tip (10, 100) and bearing cap (30, 140) center and allow a cutting tool (150) to be rotated and translated by hand, by using a handchuck, or by use of an external motor. When fitted with a cutting tool such as a drill bit (150), for example as shown in FIGS. 1, 3a, and 3b, the drill bit (150) inserts longitudinally through the body of the invention and serves to cut and grind bone cuttings (195) at its tip and translate the bone cuttings (195) up the tip into the tissue collection chamber (110).

The terms "bushing" and "bearing" are used interchangeably herein to illustrate that the surface on which a cutting tool runs can be a simple bushing, or a roller bearing that turns with the cutting tool and has no sliding contact between the surface of the tool and the bearing.

The present invention efficiently combines three processes simultaneously to channel, pull, or fling cuttings resulting from the use of cutting tools into a collection chamber. When a cutting tool is inserted through the instrument, the instrument acts independently from the cutting tool by allowing cutting tool rotation along its longitudinal axis and translation of the cutting tool in and out of the entire instrument without being required to change the speed or translational characteristics of the drill and its motor. When in use, cuttings are channeled through the action of flutes, pulled through translation of the bit, flung through centripetal forces caused by rotation of the bit, and may be withdrawn using a fourth process through evacuation of the collection chamber using suction.

A cutting tool is a tool having a flute such as, for example, a drill bit, bur, grinder, rasp, reamer, milling cutter, fluted trocar, fluted hole saw, or the like. In a further embodiment, a wiper (130, 600, 620, 640) is provided for wiping cuttings (195) from a tool (170) causing the cuttings to be deposited into the collection chamber (110) when the cutting tool is removed from the instrument. Use of a wiper adds a fifth process, that of wiping, to the herein-described processes of channeling, pulling, flinging and sucking cuttings to more efficiently and completely clear all cuttings from the cutting tool. The wiper (130, 600, 620, 640) may be designed so as to fit into the flutes (230) of the cutting tool. The wiper (130, 600, 620, 640) is concentrically oriented with the cutting tool, and may have a protrusion (160, 610, 630, 650) in its bore that reaches into the flutes (230) of a cutting tool to wipe the flutes of cuttings when the cutting tool is pulled through the wiper. The wiper (130, 600, 620, 640) is free to rotate within the collection chamber or an adjacent bearing housing during cutting tool rotation or translation through the instrument. In an embodiment having a wiper designed for a drill bit, a drill wiper (130, 600, 620, 640) turns with the drill bit (150) and allows drill bit (150) translation. The drill wiper (130, 600, 620, 640) runs on an inner bore and is contained within a wiper bushing (120). The drill flute wiper protrudes into the flutes of the drill bit to clear the flutes of bone cuttings and blood; the wiper rotates within the collection chamber during drill bit rotation and translation within the collection chamber.

Protrusions may be lobes (610, 650), hairs, wires, brushes (630), threadlike projections (630), or the like. A wiper (620) may be adapted to a tapered cutting tool. In one wiper embodiment (620), the projections (630) are like the spokes on a wheel and flexible for adaptation to tapered reamers with one or more flutes. This wiper (620) turns in the housing so as to minimize rotational action of the bit against the spoke-like protrusions (630), while allowing translation and wiping of tapered fluted bits or reamers. A reamer wiper (640) with irregular flute-shaped protrusions (65) can be used with the instrument. When flexible protrusions such as hairs, wires, brushes or threadlike projections (630) are used the wiper may be stationary. In this case the flexible protrusions conform to the surface of the drill bit and clear cuttings from the flutes.

The surgical instrument may further comprise an attachment that fits into the collection chamber that acts like a plunger (500, 510) to push bone cuttings (195) out of the collection chamber (20, 110) through the tip (10, 100) for application to a surgical site. In operation, the plunger (500, 510) is translated through the bore of the collection chamber (20, 110) to force cuttings out the tip (10, 100). The plunger face (530) is formed from pliable material and tapered at a more gentle angle than that of the collection chamber extrusion face (540) so that, upon contact, cuttings are first compressed at the periphery of the plunger face (530) to extrusion face (540) contact area. As the plunger face conforms due to its pliable material, the contact area grows in size and towards the tip (10, 100) bore. This action extrudes all materials into the tip (10, 100). The tip is cleared with the tip plunger (500) once the collection chamber plunger (510) reaches full travel.

The instrument of the present invention may further comprise an attachment containing biocompatible materials, pharmaceuticals, or biologics for mixing with bone cuttings. The attachment would fasten to the bore of the collection chamber (20, 110) and provide a means for mixing the contents of the attachment with the bone cuttings (195) within the collection chamber (20, 110). The attachment may be configured with a screen for filtering cuttings by size, or a mixer to stir the contents of the attachment with bone cuttings (195). The attachment can be used with a plunger to combine the features of facile and accurate delivery wtih the treatment of bone cuttings to enhance efficacy in facilitating bone healing.

The surgical instrument is preferably of a generally cylindrical shape, although the instrument is not limited thereto. Alternative general shapes may be elongated and shaped for ease of use such as having a grip, preferably a grip that is ergonometrically shaped. An embodiment that has been fabricated and used in surgery is a cylinder of about 1.25 inches in diameter and 4.0 inches in length. Cylinders of about $\frac{3}{8}$ to $\frac{1}{2}$ inch in diameter, and about 1 inch in length are contemplated for use with small bones; for use in industrial settings, a cylinder having a diameter of up to about 1 foot and a length of up to about 1 foot is envisioned.

Materials suitable to fabricate the instrument include, but are not limited to, stainless steel, delrin, polymethylmethacrylate, and polyethylene, for example. The tip, flute wiper, and bushing may be fabricated of metal, and is preferably made from surgical stainless steel. Alternative materials could be used, such as titanium, cobalt, or titanium nitrate coated steel. The cap, collection chamber, and wiper housing are preferably fabricated from injection-molded high density polyethylene but can be formed from polymers including but not limited to delrin, nylon, polymethylmethacrylate, polyester, polyvinylchloride, and polycarbonate. Generally, metal parts should be resistant from cutting tool wear and selected from a family of metals that is biocompatible so that a little wear debris will not adversely contaminate collected tissue. Generally, the polymer parts can be formed of any material that can be easily formed and sufficiently strong for the application.

The tip (10, 100, 103) contacts a cutting surface without penetrating into it, and serves as a cutting tool (100) guide or brace and bearing, while channeling harvested tissue into the collection chamber (20, 110). In either an embodiment having a wiper (130, 600, 620, 640) or an embodiment lacking a wiper, the instrument's tip (10, 100) forms the lower portion of the tissue collection chamber (20, 110) and may have a lip to enhance stability and retention in the collection chamber. The tip provides a pathway and means to move cuttings into the collection chamber (20, 110). The tip (10, 100) has means to eliminate slippage on bone and trap bone cuttings (195) in the cutting tool flute (170) to channel the bone cuttings up the tip (10, 100) and into the collection chamber (20, 110). In preferred embodiments, the tip has a length of 0.5" to about 5", with a tip length of about 0.5", 1.5", or 2.5" being most preferred.

A serrated edge or sharp tip teeth (15, 106) located directly on the cylindrical portion of the tip (10, 100) or on a swivel tip (180) held with elastic tip fixation prongs (183) can be used to eliminate slippage and channel bone cuttings (195). A swivel tip (180) rotates about the lower end of an optional spherically ended tip (103) so as to provide good cortical bone (193) contact.

The collection chamber body (20, 110) may attach to a cap (30, 140) or to a wiper bushing (120). When fabricated to attach to a cap (30), the open end of the collection chamber (20, 110) may have a positive lip on the internal diameter to lock with the cap. The collection chamber (20, 110) requires no moving parts and takes advantage of the movement of cuttings up cutting tool flutes, pulling of tissue through the tip and slinging of cuttings to deposit cuttings in the collection chamber. The collection chamber (20, 110) can be further enhanced by having an opening for connection to suction (401) to facilitate the collection of cuttings and to facilitate collection of blood. The collection chamber (20, 110, 401) may have a means of measuring collected tissue volume not limited to a volumetric marking, or transparent or translucent outer walls which together with a volumetric marking, can be used to measure unpacked volume. A plunger (500, 510) may be used to compress said bone cuttings for the measurement of packed volume.

The cap (30, 140) may attach to the collection chamber (20, 110) or to a wiper bushing (120). The cap (30, 140) may have a groove on the outside diameter near one end to lock with a lip in the bore of the collection chamber (20, 110); other types of connections may be threads, o-rings or a quick disconnect member. The cap (140) may house a flute wiper (130) that is held in through the use of a press-fit cylindrical bearing.

An embodiment of the invention is shown in FIG. 3a in contact with cortical bone (193) prior to drilling. The invention is shown in operation in FIG. 3b with cortical bone (193) and cancellous bone (190) being drilled and bone cuttings (195) moving up the drill flutes (170) and being deposited in the collection chamber (110).

Figure 10:
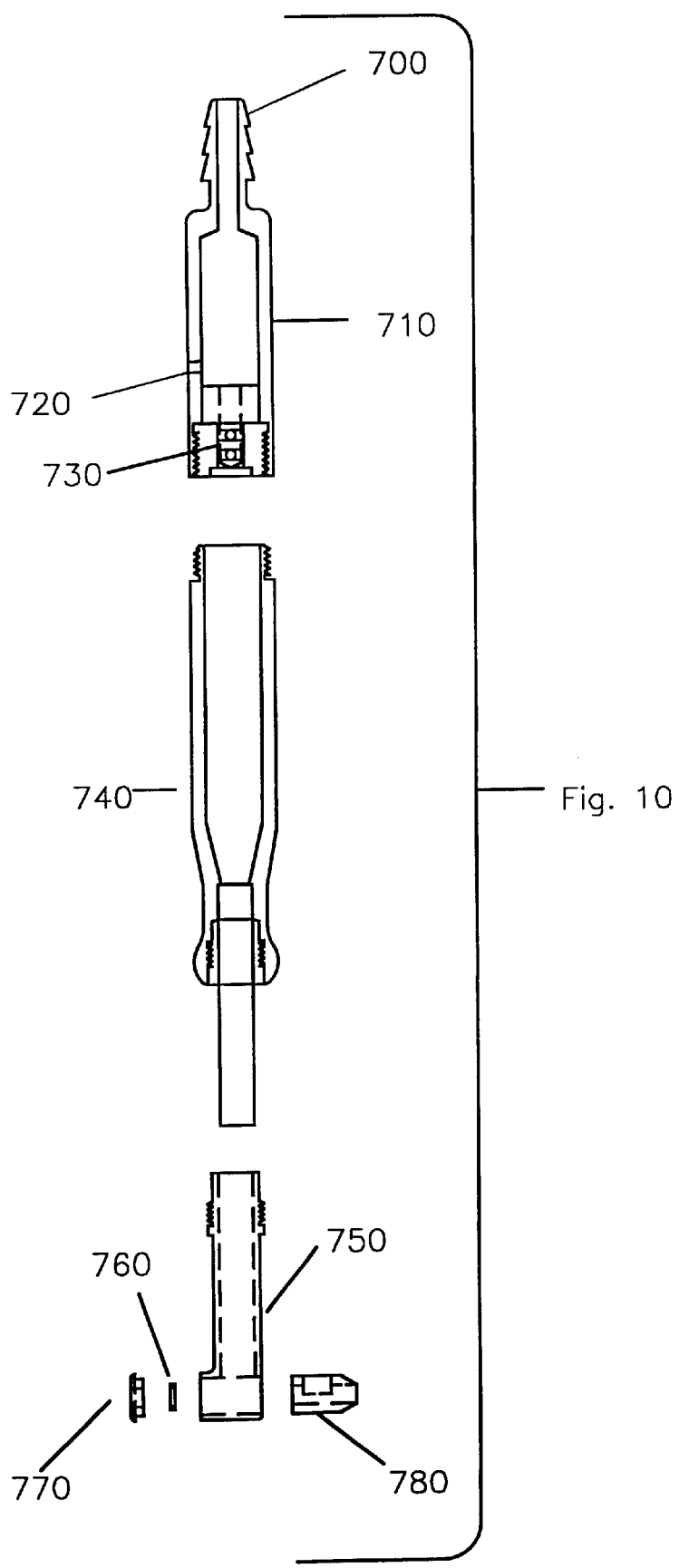
FIG. 10 shows an exploded plane view of components of an angled embodiment of the invention designed for use with suction and for surgery at sites having limited access.

A further embodiment of the present invention is described for use with suction and for surgical sites with limited access. This version of the device is shown in FIG. 10 and includes a suction port (700) for connection to a suction hose, and a handle (710) with baffle (730) and suction relief hole (720). This handle attaches to a first end of collection chamber (740). A second end of collection chamber (740) connects to collection chamber extension (750) (as used herein, a collection chamber extension forms part of and is part of a collection chamber) that incorporates a bore for a fluted tool, and includes tip (780), wiper (760), and wiper bushing cap (770). When in use, a suction hose is connected to suction port (700), and a drill bit is introduced through bushing cap (770), wiper (760), collection chamber extension bore, and tip (780) so that when drilling bone, the bit turns and translates within tip (780).

When drilling bone and marrow using this "angled" embodiment, tissues move up the flutes of the drill bit through an enclosed channel formed by the drill flutes and the bore of tip (780). The pumping action of the drill flutes, drill translation, flinging of tissue, and suction cause cuttings to be drawn into collection chamber (740) which also forms a handle. Collection chamber (740) has baffle (730) and suction relief hole (720) for withdrawing fluid from collected tissue and minimizing loss of bone cuttings into the suction tube.

Figure 5A:
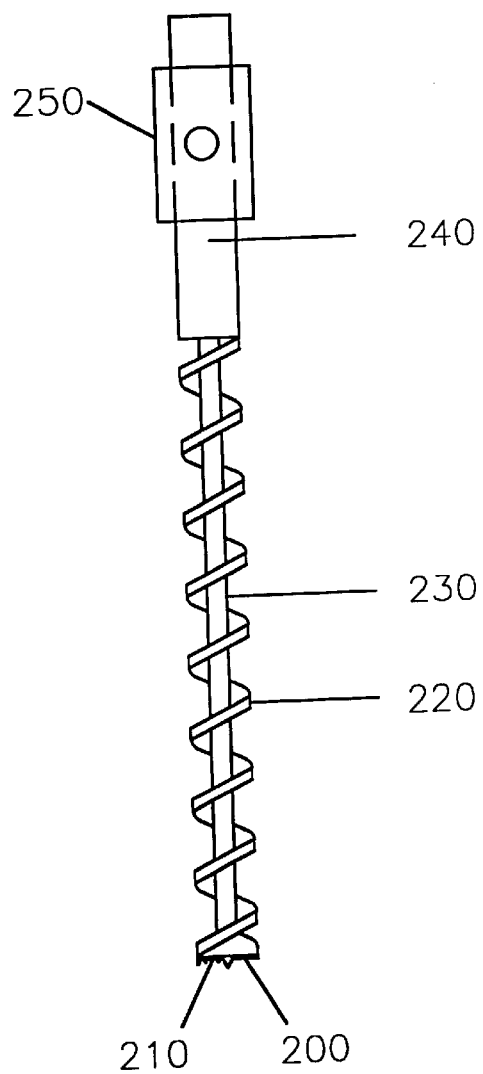
FIGS. 5a and 5b show a plane view of a fluted drill bit design that combines both grinding and cutting processes at the tip to optimize the morphology of cuttings and a large flute with low flute angle to facilitate movement of cuttings up the drill and within the tip (100).
Figure 5B:
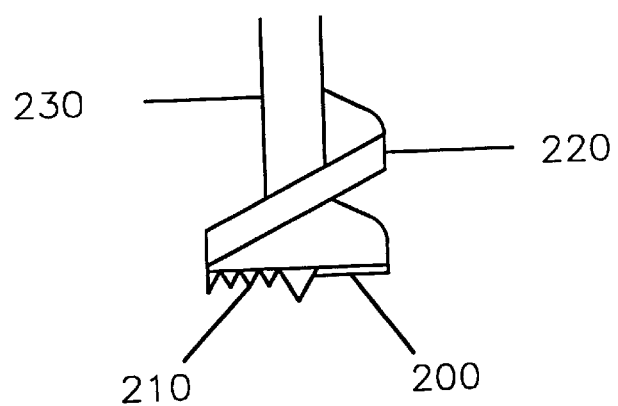
Figure 6:
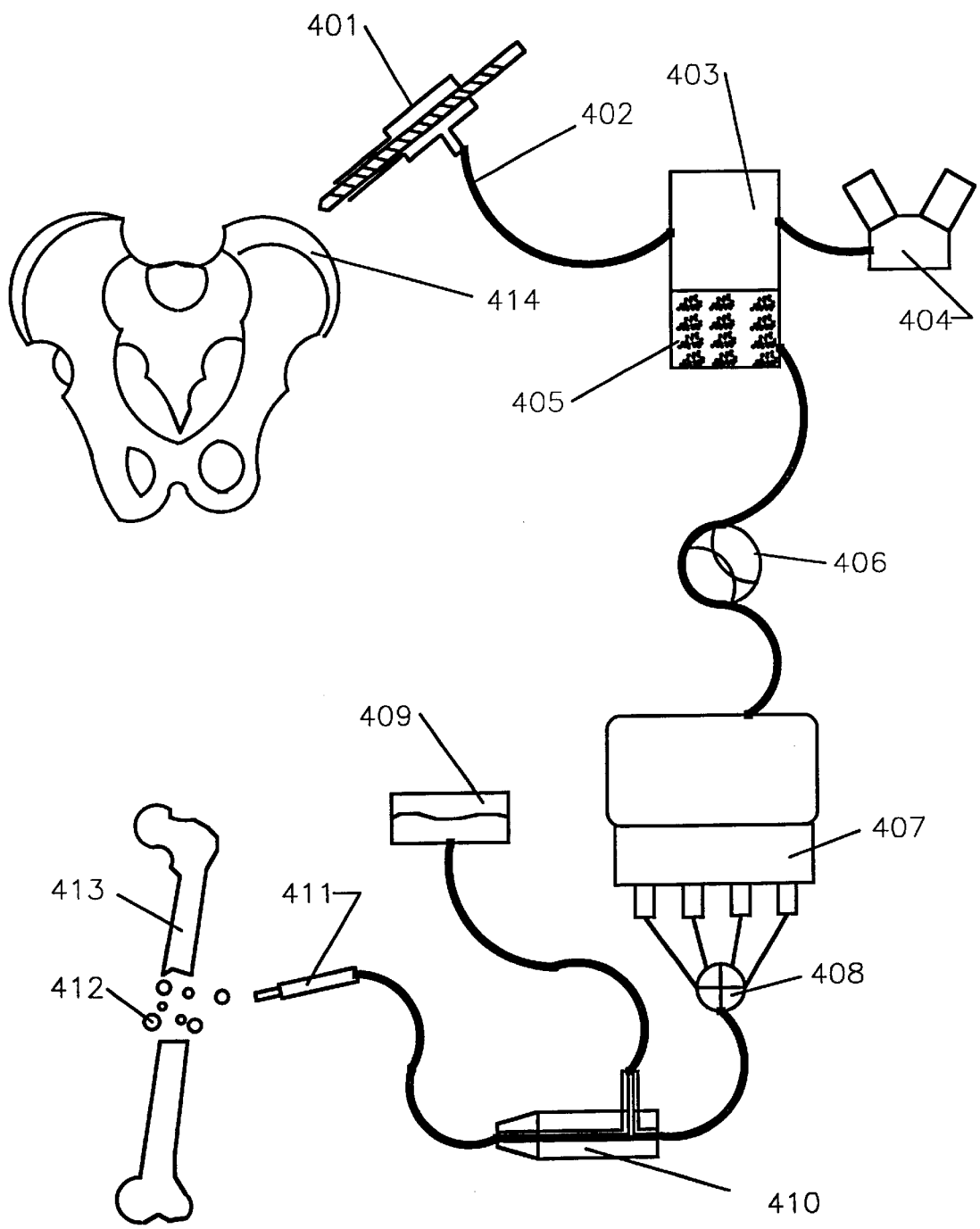
FIG. 6 shows a schematic of an embodiment of the invention that provides for aseptic tissue transplantation from a first site to a second site using an instrument of the present invention. Harvested tissue may be processed to further enhance its bone inductive potential.
Figure 7:
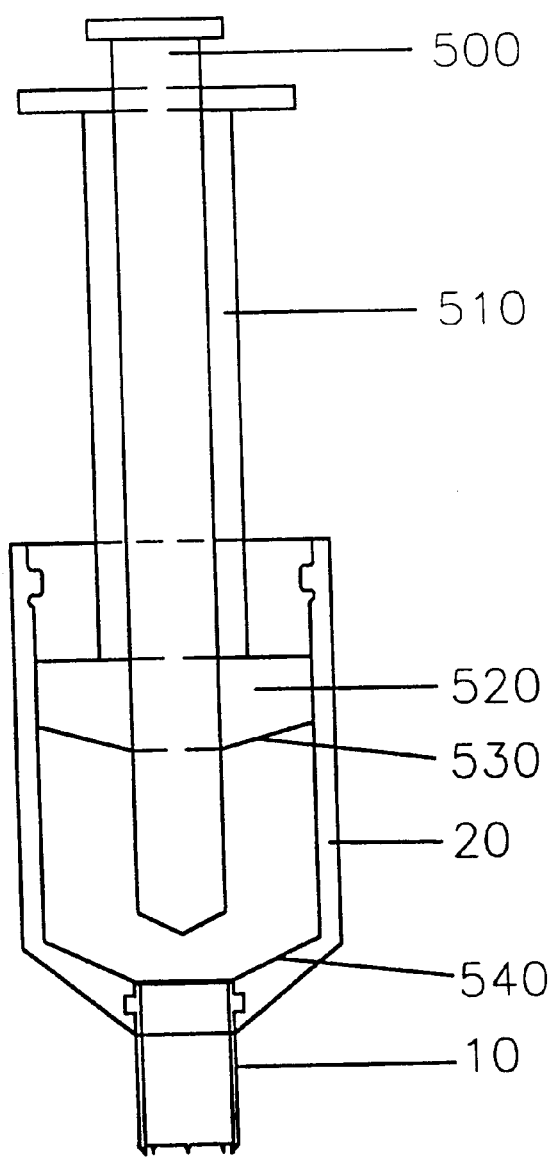
FIG. 7 shows a dual plunger attachment within a collection chamber of an instrument of the present invention for extrusion of collected cuttings.
Figure 8:
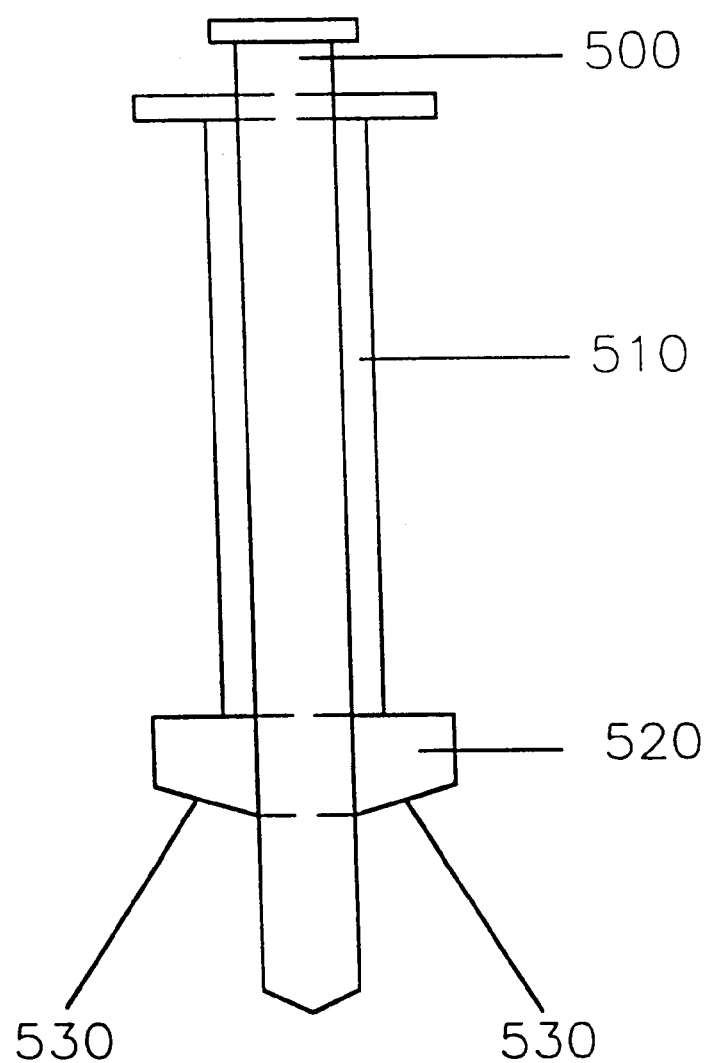
FIG. 8 shows a cross-sectional view of a dual plunger.
Figure 9A:
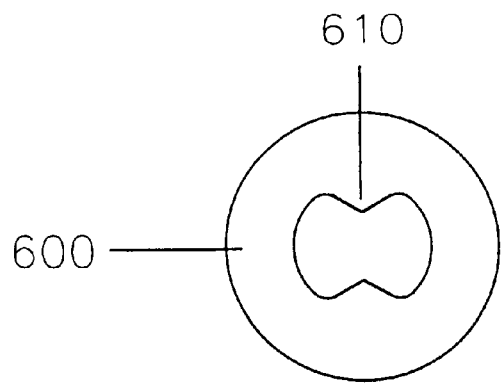
FIG. 9a shows a top view of a rotating drill flute wiper (600) with rigid flute protrusion (610) for drill bits with two conventional flutes.
Figure 9B:
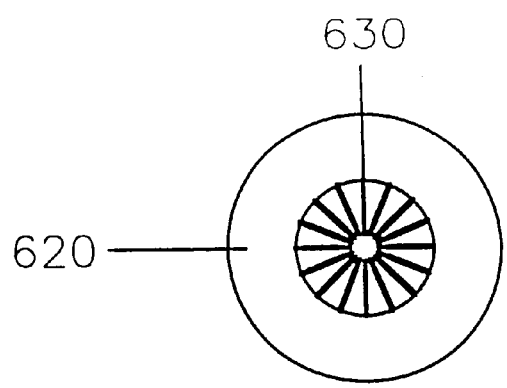
FIG. 9b shows a top view of a rotating generic wiper (620) with flexible bristle-like protrusions (630) for use with a drill bit, tapered reamer, bur, rasp, or saw.
Figure 9C:
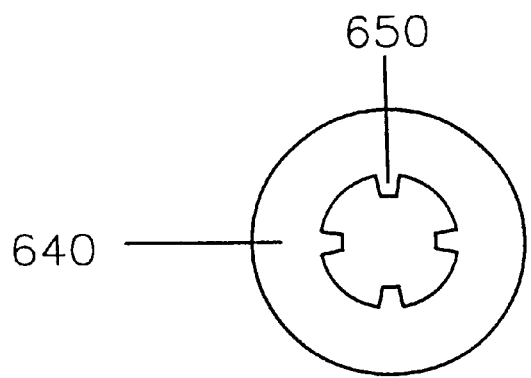
FIG. 9c shows a top view of a rotating reamer flute wiper (640) with rigid or flexible flute protrusions (650) for a multifluted reamer.

In one aspect of the invention, the surgical instrument is designed for use with a drill bit. A drill bit having a tip that both grinds and cuts bone (200, 210) to optimize the size of bone particles for specific transplantation purposes is an aspect of the invention (FIGS. 5a and 5b). The bit tip has teeth (210) and a cutting edge (200) at the entry to its flutes to grind and cut bone while creating a bore in bone. The teeth and cutter geometry can be chosen to adjust the particle size of bone cuttings. The drill may have a large flute volume and low flute angle to facilitate bone cutting movement into the tissue collection chamber.

Drill bits of most any design may be used, and the quality of the bone cuttings (195) can be optimized through the use of a specialty bit in one embodiment. The cutting edge of a specialty drill bit tip has a straight cutting edge (200) on one side, and has a row of grinding teeth (210) on the other side. The grinding teeth (210) protrude from the tip of the drill beyond the cutting edge (200) and serve to grind and loosen material for the cutting edge (200) to sever and scrape into the entry to the flute (230).

Further aspects of a drill bit that are contemplated as part of the present invention include the following. A land (220) can be optimized for different applications using different flute volumes and angles to translate bone cuttings (195) or marrow tissue. A drill shank (240) without fluted section attaches to a drill motor and serves to stop translation of the drill through the drill wiper (130) through interference between the flute wiper (160) and unfluted section of the drill shank (240). The drill shank (240) can be fitted with a calibrated adjustable stop to allow precise control of drill penetration depth.

The surgical instrument may be a single use device, i.e., a disposable unit that is provided in a sterile package to a user. Models adapted to fit drill bit diameters of 2–4 mm, 4–6 mm, 6–8 mm, and 10–12 mm are contemplated. In particular, models adapted to fit drill bit diameters of 5, 6, 7, 8, 9, or 10 mm are preferred.

Figure 11:
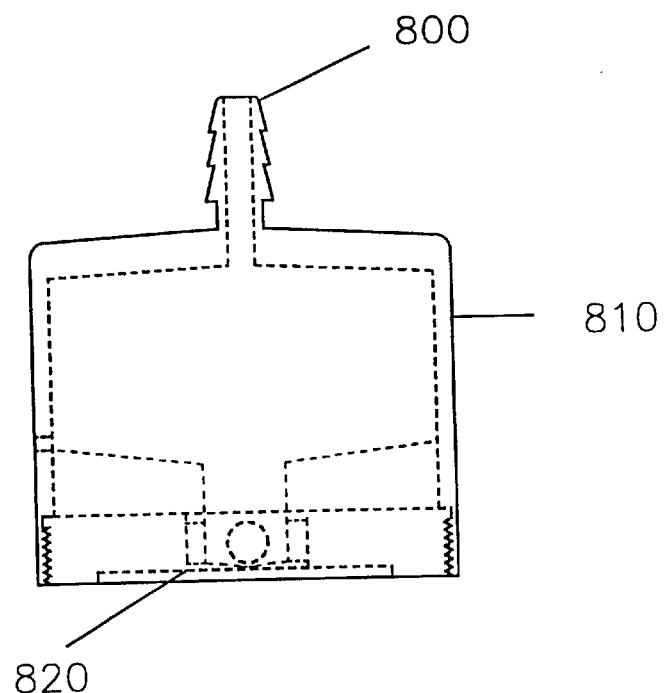
FIG. 11 shows a suction attachment for a materials collection system of the present invention.
Figure 12:
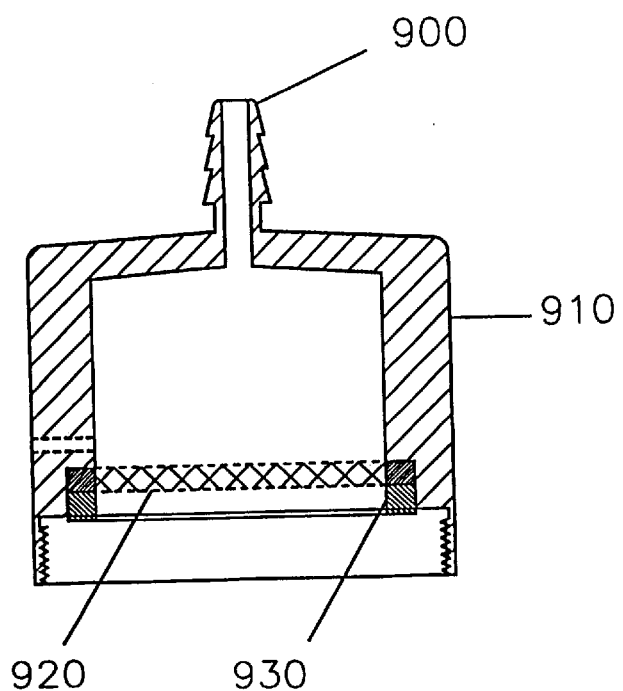
FIG. 12 shows a further embodiment of a suction attachment for a materials collection system of the present invention.

Once bone has been collected from the flutes of the drill the bony site can be aspirated through the use of a suction attachment (810, 910), shown in FIG. 11 and FIG. 12. This suction attachment (810, 910) replaces wiper bushing cap (30,140) of FIGS. 1–4b, once the drill bit has been removed from the instrument. The suction attachment can be removably connected to the collection chamber with tabs, grooves, threads, a structure allowing a press fit, or the like. Once connected, a suction hose can be connected to suction port (800, 900) or suction attachment (810, 910). This configuration allows the instrument to act as an aspiration instrument to clear bone chips and marrow tissues that were not cleared from the site during drilling. This suction attachment (810, 910) restricts the loss of bone and marrow tissue out of suction port (800, 900) through the use of a baffle (820), or filter (920). Baffle (820) may consist of barriers designed to trap particles and allow fluid to be cleared from the instrument. A screen or filter (920) held in position by seal ring (930) may be used instead of, or in conjunction with, baffle (820) to selectively retain large particles while allowing small particles to pass out of suction port (800, 900).

Another embodiment of the invention includes the surgical instrument described herein and further includes means for transferring harvested tissue to a second site with optional processing of the harvested tissue. In this embodiment, the collection chamber (401) is connected to a suction line (402) to move bone cuttings (405) and fluid collected from a surgical site, such as the iliac crest (414), so that it can be stored in a tissue reservoir (403). Vacuum is supplied to the system by a vacuum pump (404) connected to the tissue reservoir (403). Collected material in the tissue reservoir (403) is moved using a roller pump (406) to a tissue separator (407). The tissue separator (407) can contain screens, filters, centrifuge units, or other cell and tissue separating devices as well as acid and basic solutions to modify the collected tissue. The tissue transplant system may comprise a pump, filter, centrifuge, mixing chamber, settling chamber, conduit, or the like. The system may have an applicator for the implantation of collected skeletal tissue. Skeletal tissue may be harvested from a variety of sites, such as rib, fibula, iliac bone, cranium, sternum, tibia, or the like.

For example, a centrifuge may be used to fractionate the harvested tissue and remove red and/or white blood cells; or harvested tissue may be chemically washed so as to increase the bone-inductive potential of various proteins and cells while maintaining their viability. Processing may include steps to enhance the bone-forming potential of said bone cuttings; the steps including but not limited to filtering, rinsing with water, grinding of said bone cuttings, washing with acid solutions, or washing with basic solutions.

Processed tissue components can be combined or sent separately to the site of implantation through a valve (408) to an encapsulation nozzle (410) where an encapsulant such as algin, poly-L-lysine, collagen, polylactic acid, polyglycolic acid, methylcellulose, glycerol, saline, calcium phosphate, or calcium carbonate from an encapsulant reservoir (409) can be combined with the tissue. Encapsulant with tissue (412) or tissue alone can then be applied at a bone (413) defect site with an applicator (411). A positive displacement pump (406) provides the positive pressure to move the material through the processing stage and to the implant site.

Cancellous bone is cell-rich and integrates rapidly with recipient bone and is resistant to infection. In comparison with solid bone grafts, particulate or paste-like bony materials offer considerable advantages. Further advantages of fresh autograft bone chips or particles include; high graft surface area facilitating vascularization and remodeling, healing would occur as a "field phenomenon" occurring simultaneously throughout the entire defect, irregularly shaped defects can be filled more completely with contact between host site and graft tissues closer and more extensive, and only a small surgical access is necessary to fill a large bone cavity defect. Furthermore, bone cells within cancellous bone graft material placed in contact with a well-vascularized recipient bed will survive, and storage of harvested cancellous bone material in normal saline ensures cell survival in the 95% to 100% range even after a working time of up to four hours (Marx R. et al. *J. Oral Surg.* 37:712–718, 1979).

An aspect of the invention is the use of the herein described tissue transplant system combined with the addition of growth factors and matrix material to enhance bone wound healing. Addition of such factors and material is expected to optimize the state of the harvested skeletal tissue. Such factors and material include, for example, transforming growth factor beta and alpha, bone morphogenetic protein, platelet derived growth factor, epithelial growth factor, fibroblast growth factor, vascular permeability factor, mitogens, mesenchymal cells, progenitor cells, or natural bone matrix.

Procurement of tissue may be separated in time by implantation into the donor or into a different recipient. One of skill in the art would realize, in light of this disclosure, how to use the instrumentation of the present invention when tissue is harvested from one patient and implanted into a different patient.

In the operation of the invention, drilling of skeletal tissue for reconstructive surgery, or for placement of orthopaedic, dental, oral, or maxillofacial implants such as plates, screws, or rods is performed using aseptic technique. The drill cuttings are commonly discarded; with use of the present invention, the drill cuttings are collected and can be placed around the implant to further anchor the implant and facilitate healing. The invention is used in conjunction with common drill bits and drill motors.

The method involves aseptic collection and transfer of bone cuttings and/or marrow constituents for immediate transplantation. Tissue collected from use of the surgical instrument provided by the present invention is cortical and cancellous bone combined with marrow tissues and blood that form a paste-like graft material. This material has paste-like handling properties, high surface area, and a generally open structure. These features of the methods of the present invention facilitate handling, vascularization, modeling, and provide a bone-inductive scaffolding for enhancement of healing of a surgical site.

In practice of a preferred embodiment, a drill bit (150) is inserted through the cap (140), wiper bushing (120), drill wiper (130), collection chamber (110) and tip (100). Rotation of the drill bit (150) cuts bone. Bone cuttings (195) are confined within the drill flute (170) by the tip (100). Continued rotation of the drill bit (150) causes translation of the bone cuttings (195) up the inner bore of the tip (100). Bone cuttings (195) that have moved up the tip (100) and into the collection chamber (110) fall from the drill flutes (170) and collect in the collection chamber (110). Bone cuttings remaining in the drill tip (10, 100) can be pulled into the collection chamber (20, 110) through drill bit translation and cuttings remaining in the drill flutes (170) are removed from the drill flutes (170) by centripetal force, suction, or the drill wiper (130).

The drill wiper (130) is free to rotate in the wiper bushing (120) along its common axis with the drill bit (150). The flute wiper (160) of the drill wiper (130) extends into the drill flute (170) to wipe any residual bone cuttings that have not collected in the collection chamber (110). The drill wiper (130) turns with the drill bit when it is rotated along its long axis or when the drill bit is translated through the tip (100), collection chamber (110) and drill wiper (130).

The tip (100) is connected to the tissue collection chamber body (110). The collection chamber (110) connects to the wiper bushing (120) which serves as a bearing surface and guide for the drill wiper (130). The drill wiper (130) rotates freely in the wiper bushing (120) and is confined by the cap (140) which is connected to the wiper bushing (120). The tip (100), collection chamber (110) and wiper bushing (120) can be combined into one part and fabricated as a disposable instrument.

The surgical instrument is used with conventional surgical drill bits. A drill bit of the appropriate diameter, flute length and overall length is inserted into the appropriate model of the surgical instrument from the cap end. The instrument is held in one hand and the tip positioned on bone at the point of drilling. As bone is drilled, bone and/or marrow tissue fragments are carried up to the flutes of the drill bit, through the tip and passively fall from the flutes into the collection chamber. The drill bit can extend beyond the tip of the instrument up to about 3–5 inches, and the instrument may be moved in an arc motion so as to harvest tissue from a cone-shaped area of the bone. When the drill bit is translated longitudinally away from bone within the instrument in and out of the tip, rotating action further acts to displace material from flutes into the collection chamber, and in an embodiment having a wiper, movement of the drill bit through the wiper serves to displace material into the collection chamber.

Placement of the materials collection system of the present invention through skin and other soft tissue to a site of bone surgery may be accomplished using a fluted trocar cutting tool in combination with the materials collection instrument. The fluted trocar is a sharped-tip cylindrical cutting tool and is introduced into the materials collection instrument so that the sharp cutting tip of the trocar extends past the tip of the collection system. The positioned trocar and instrument are pushed through soft tissue until the trocar contacts bone. Once positioned on bone, the trocar is removed and a fluted cutting tool is introduced into the instrument for bone surgery.

The description of the embodiments and their operation is given not to limit the design and scope of the invention but to broaden the description of the invention to include any method or device that uses a surgical instrument of the present invention and achieves the goal of harvesting and processing of bone or marrow tissue for the purpose of transplantation.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following example is included to demonstrate a preferred embodiment of the invention. It should be appreciated by those of skill in the art that the techniques disclosed in the example represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Collection of Skeletal Tissue

A surgical instrument according to the present invention was built and tested in a cadaver and in living animals. The device was used with a conventional drill bit in fresh cadaver femoral bones. Bone cuttings were collected following a few revolutions of the drill bit. Cuttings moved up the flute within the confines of the tip. Cuttings exited the flute once they passed the tip and entered the collection chamber. The white color of cortical bone was seen through the collection chamber window and cancellous chips were coated with a small quantity of blood. Six 0.272 inch holes of approximately 2 cm depth were made. With each new hole the collection chamber continued to fill. The large quantity of osseous tissue collected in the chamber quickly obscured the view of the drill.

While drilling, the flutes were noted to retain some of the cuttings. To test the performance of the flute wiper, the drill bit was withdrawn. When removed from the device, the flutes were noted to be clear of cuttings and the cuttings were seen to fall into the collection chamber. The action of the rotating wiper was smooth and did not cause the bit to bind during drilling or withdrawal. At the desired drill depth, the bit could be quickly pushed in and pulled out to collect additional osseous tissue from the margins of the drill hole, or to pump blood into the collection chamber that was hemorrhaging into the site. Use of a vacuum in conjunction with the device could facilitate collection of more blood if clinically advantageous. Once drilling was completed, the drill bit was withdrawn for the final time.

In one embodiment of the invention, the cap and wiper bearing are fabricated as one unit, and this unit may be removed together with the rotating flute wiper. The collection chamber and tip also may be fabricated as one piece. A plunger assembly will connect to the collection chamber and facilitate clearing of the harvested osseous tissue from the device. This plunger assembly would allow harvested osseous tissue to be forced from the collection chamber through the tip to facilitate application to a site of injury, fusion, or implantation. With plunger assembly attached, the device allows placement of collected osseous tissue and blood.

Following collection, the collection chamber was emptied of osseous tissue. The osseous tissue was noted to consist of coarse cuttings with varied dimensions of approximately 0.5 mm ×4 mm ×8 mm. Blood coated the cuttings, however, no free liquid was present in the collection chamber.

Tissue was evaluated for volume and the values were compared to theoretical values based on the dimensions of the drill hole; tissue was also evaluated for weight and those values were compared to theoretical weight which was calculated using the density of the bone segment multiplied by the volume of the drill hole. The tissue collection data are provided for volume comparisons in Table 1, and for weight comparisons in Table 2.

TABLE 1

Tissue Collection Comparison By Volume

| Sample Number | Harvested Tissue Volume (cc) | Theoretical Tissue Volume (cc) | Harvested Tissue as a % of Theoretical |
|---|---|---|---|
| 103951 | 0.65 | 0.65 | 100 |
| 103952 | 0.62 | 0.60 | 103 |
| 103953 | 0.60 | 0.54 | 111 |
| 103954 | 0.58 | 0.53 | 109 |
| 103955 | 0.56 | 0.58 | 97 |
| 103956 | 0.59 | 0.60 | 98 |
| 103957 | 0.60 | 0.61 | 98 |
| 928951 | 0.80 | 0.71 | 112 |
| 928952 | 0.31 | 0.30 | 103 |
| 928953 | 0.26 | 0.26 | 100 |
| 928953 | 0.29 | 0.30 | 96 |
| 102951 | 2.4 | 2.6 | 93 |

TABLE 2

Tissue Collection Comparison By Weight

| Sample Number | Harvested Tissue Weight (grams) | Theoretical Tissue Weight (grams) | Harvested Tissue as a % of Theoretical |
|---|---|---|---|
| 103951 | 0.55 | 0.98 | 56 |
| 103952 | 0.54 | 0.93 | 58 |
| 103953 | 0.53 | 0.88 | 60 |
| 103954 | 0.50 | 0.85 | 59 |
| 103955 | 0.49 | 0.85 | 58 |
| 103956 | 0.50 | 0.89 | 56 |
| 103957 | 0.54 | 0.91 | 59 |
| 102951 | 3.1 | 3.1 | 100 |

The surgical instrument was used in a living animal in both iliac crest and proximal tibial metaphysis sites. Two holes were drilled in each location. The observations made during the drilling of fresh cadaver bone and the sites in the live animal were consistent. Osseous tissue collection was achieved with the bone cuttings having a light coating of blood. Blood in the collection chamber was not of sufficient quantity to form free liquid. The two drill holes in the tibia produced 0.45 cc or 0.48 grams of bone. The two drill holes in the iliac crest produced 0.91 cc or 1.09 grams of bone.

These data demonstrate that the surgical instrument of the present invention is straightforward to use and allows collection of vital osseous tissue for placement at an injured site. With the use of this device, a hole drilled in bone to fasten an implant or place a screw can be a source of highly inductive tissue capable of enhancing the healing response of bone, filling large bone defects, or facilitating fusion of unstable or diseased joints.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An instrument for collection of cuttings, comprising:
    a tip having a bore for fitting to a cutting tool having a flute, wherein when fitted with a cutting tool having a flute, the tip and the flute form an enclosed channel; and
    a collection chamber attached to the tip for collecting and holding cuttings;
    a cutting tool having a flute fitted through the bore of the tip and translatable in and out through the instrument;
    wherein when in use, the instrument allows continuous unidirectional cutting tool rotation and cutting tool translation in and out through the instrument so as to channel, pull, or fling cuttings for accumulation in the collection chamber.

2. The instrument of claim 1 is further comprising a cap attachable to the collection chamber, the cap adapted for use with a cutting tool.

3. The instrument of claim 1 or 2 wherein the cutting tool is a concentrically oriented cutting tool.

4. The instrument of claim 3 wherein the cutting tool is selected from the group consisting of a drill bit, bur, grinder, rasp, reamer, milling cutter, fluted trocar, and a fluted hole saw.

5. The instrument of claim 3 wherein the cutting tool is a drill bit.

6. The instrument of claim 3 wherein the cutting tool is fitted with an adjustable stop.

7. The instrument of claim 3 further comprising means for rotating the cutting tool.

8. The instrument of claim 7 wherein the means for rotating the cutting tool is an external motor.

9. The instrument of claim 2 wherein the collection chamber further comprises an opening for connection to a vacuum line.

10. The instrument of claim 1 or 2 further comprising an attachment for processing cuttings.

11. A materials transplant system comprising:
    the instrument of claim 1; and
    means for moving cuttings to a site of implantation.

12. The materials transplant system of claim 11 wherein the system is sterile.

13. The materials transplant system of claim 11 wherein the materials are tissue cuttings and the system further comprises means for processing tissue cuttings.

14. The materials transplant system of claim 13 wherein means for processing tissue cuttings comprises an encapsulation nozzle.

15. The materials transplant system of claim 11 wherein the collection chamber further comprises an opening for connection to a vacuum line.

16. A method for aseptically transplanting skeletal tissue from a first site to a second site comprising
    harvesting skeletal tissue from a first site using the materials transplant system of claim 12; and
    aseptically transplanting harvested tissue to a second site.

17. The method of claim 16 further comprising the step of processing harvested skeletal tissue before transplanting at the second site.

18. The method of claim 17 wherein the processing is washing, grinding, filtering, separating, acid addition, base addition, encapsulant addition, pharmaceutical addition, or growth factor addition.

19. The method of claim 16 wherein the first site and the second site are within one subject.

20. A method for collection of cuttings of bone, metal, a ceramic, or a polymer, comprising assembling the instrument of claim 1; and harvesting cuttings of bone, metal, the ceramic, or the polymer into the collection chamber thereby, collecting the cuttings.

21. The method of claim 20 further comprising the step of flushing the collection chamber of the instrument with an inert gas for minimizing combustion hazard.

22. A method for collection of cuttings in a microgravity environment, comprising assembling the instrument of claim 1; and harvesting cuttings in a microgravity environment into the collection chamber thereby, collecting the cuttings.

23. An instrument for collection of cuttings, comprising:

a tip having a bore for fitting to a drill bit having a flute, wherein when fitted with a drill bit having a flute, the tip and the flute form an enclosed channel;

a collection chamber attached to the tip for collecting and holding cuttings; and a drill bit having a flute fitted through the bore of the tip and translatable in and out through the instrument, wherein when in use, the instrument allows continuous unidirectional drill bit rotation and drill bit translation in and out through the instrument so as to channel, pull, or fling cuttings for accumulation in the collection chamber.

24. The instrument of claim 1, 2, or 23 wherein the tip further comprises a tooth.

25. The instrument of claim 1, 2, or 23 wherein the tip is a spherical tip.

26. The instrument of claim 1, 2, or 23 wherein the tip is a swivel tip.

27. The instrument of claim 1, 2, or 23 wherein the collection chamber further comprises a means for measuring volume.

28. The instrument of claim 27 wherein the collection chamber has a transparent or translucent wall and the means for measuring volume includes a volumetric marking on the wall.

29. The instrument of claim 1, 2, or 23 wherein the tip and the collection chamber are fabricated as one unit.

30. The instrument of claim 1, 2, or 23 wherein the collection chamber is positioned at an angle with respect to the tip.

* * * * *